US006427696B1

United States Patent
Stockhausen

(10) Patent No.: US 6,427,696 B1
(45) Date of Patent: Aug. 6, 2002

(54) ANTI-SNORING DEVICE

(76) Inventor: Rolf Stockhausen, Immermannstr. 10, D-40210 Dusseldorf (DE)

(*) Notice: Subject to any disclaimer, the term of this patent is extended or adjusted under 35 U.S.C. 154(b) by 0 days.

(21) Appl. No.: 09/677,206

(22) Filed: Oct. 2, 2000

(30) Foreign Application Priority Data

Oct. 11, 1999 (EP) .............................. 99120235

(51) Int. Cl.$^7$ ................................. A61F 5/56
(52) U.S. Cl. ................. 128/848; 128/859; 602/902
(58) Field of Search ............... 128/848, 859–862; 602/902; 433/6

(56) References Cited

U.S. PATENT DOCUMENTS

| 648,028 A | * | 4/1900 | Hooper ................. 128/848 |
| 2,479,780 A | * | 8/1949 | Remensnyder ............ 433/6 |
| 4,350,154 A | | 9/1982 | Feldblau |
| 5,462,066 A | | 10/1995 | Snyder |
| 5,499,633 A | | 3/1996 | Fenton |
| 5,666,973 A | * | 9/1997 | Walter ................. 128/861 |
| 5,816,802 A | * | 10/1998 | Montgomery ............ 128/861 |
| 6,055,986 A | | 5/2000 | Meade |

FOREIGN PATENT DOCUMENTS

| DE | 666588 | 11/1938 |
| DE | 195 45 562 A1 | 6/1997 |
| DE | 197 06 204 C2 | 2/2000 |
| EP | 0 371 889 A1 | 6/1990 |
| EP | 0 815 813 A1 | 1/1998 |

* cited by examiner

Primary Examiner—Michael A. Brown
(74) Attorney, Agent, or Firm—Maurice L. Miller, Jr.

(57) ABSTRACT

An anti-snoring device is disclosed featuring a curved cover plate which can be inserted between the lips and teeth of a person in order to cover the tooth spaces. A pair of projections extending from a concave surface of the plate are directed so as to engage behind the teeth of the upper and lower jaw. The device may be made of a plastisizable material so that the plate and its projections can be pressed intimately against the tooth surfaces by tongue or finger pressure so as to envelop both the teeth and regions of the gums adjacent thereto.

14 Claims, 2 Drawing Sheets

ANTI-SNORING DEVICE

The present invention concerns an anti-snoring device with a curved cover plate having a convex and a concave side which is insertable into the space between the lips and teeth of a person in order to cover the tooth spaces, there being configured on the concave side a mandibularly directed projection as well as a palatally directed projection which, in the inserted state, engage behind the teeth of the upper and lower jaws, and the material of the anti-snoring device being made at least locally of a plasticizable material, so that the cover plate as well as the projections can be pressed intimately against the tooth surfaces by tongue pressure or finger pressure. The invention further concerns a method for molding an anti-snoring device of this kind.

Snoring in human beings is caused by the fact that when breathing occurs through the mouth, the respiratory airflow causes the soft parts of the pharynx, the uvula, the soft palate, and the rear portions of the tongue to vibrate. This occurs predominantly when the upper respiratory passages are constricted and the airflow is thereby accelerated.

One circumstance in which constriction of this kind occurs is when the tongue falls back into the pharyngeal cavity. A number of anti-snoring devices have therefore been designed that are aimed at preventing this falling movement of the tongue during sleep (DE-C-666 588), or at displacing the lower jaw and thus the tongue forward, so as thereby to keep the respiratory passages open.

U.S. Pat. No. 5,462,066, for example, discloses an anti-snoring device of the aforesaid kind whose purpose is to immobilize the lower jaw in a pulled-forward position. This anti-snoring device has a cover plate that is insertable into the space between the lips and teeth of a person, there being provided on the concave side of the cover plate, facing toward the interior of the mouth, a mandibularly directed and a palatally directed projection that, in the inserted state, engage behind the teeth of the upper and lower jaws in such a way that the lower jaw is immobilized in a pulled-forward position. This anti-snoring device is manufactured by heating a blank of the anti-snoring device that is made of a thermoplastic material and thereby plasticizing it. Following insertion of the soft blank into the mouth, the cover plate and the projections are molded with the lower jaw displaced forward, in order to adapt the shape of the blank to the patient's mouth.

In a further anti-snoring device of this type that is known from DE 197 06 204 A1, it is additionally proposed to configure the cover plate in such a way that it covers both the tooth spaces of the incisors and the tooth spaces of the molars, so that the oral cavity is completely sealed off from the outside. The result of this embodiment is that it is no longer important for the edge of the mouth to rest sealingly on the convex side of the cover plate. Thus after insertion of the anti-snoring device, a suction reflex results in a high level of negative pressure which keeps the tongue drawn firmly against the inner side of the teeth. This in turn keeps the respiratory passages in the pharyngeal cavity open, so that the velocity of the respiratory airflow remains low, and the soft tissues are thus no longer caused to flutter. Because of the gapless seal, the negative pressure is maintained for a long period.

The known anti-snoring devices have proven entirely successful. Efforts are nevertheless being made to improve the anti-snoring device further and to enhance its effectiveness.

It is therefore the object of the invention to create an anti-snoring device of the kind cited initially that effectively prevents snoring. A method for manufacturing such an anti-snoring device is also to be described.

According to the present invention, this object is achieved in that the cover plate as well as the projections are configured such that they envelop both the teeth and the regions of the gums adjacent thereto, and are made of a material that possesses an adhesive effect in the non-plasticized state.

The underlying idea of the invention is to create an anti-snoring device that is exactly adapted to and molded onto the patient's teeth and jaw. This almost airtight inclusion of the upper and lower jaw teeth in a block of material prevents the jaws from involuntarily sliding apart, and thus prevents the tongue and lower jaw from sliding back. An involuntary suction motion is also made possible, with the result that the tongue is immobilized in a forward location by the negative pressure behind the teeth.

To manufacture an anti-snoring device of this kind, a mold made of soft material is introduced into the mouth, where the material is then adapted to and molded onto the teeth and the jaws by tongue pressure and finger pressure, thus resulting in intimate enveloping of the upper and lower rows of teeth on both the outside and inside. Following solidification of the material, which in this context should substantially neither shrink nor expand, the teeth can be detached from this exact negative mold of the jaws only by vigorously and deliberately opening the jaws.

Manufacture of this anti-snoring device is preferably accomplished by the fact that after the soft form of the anti-snoring device is introduced into the mouth, a deep bite is taken into the soft material, with the lower jaw thrust moderately forward, in such a way that the incisors, canines, and optionally also the molars penetrate deeply into the material, but without biting through the material. The lower jaw then remains in a thrust-forward position, and there remains between the material of the cover plate and the projections a web-like connection—the bite strip—having a thickness of approximately 1 cm between the material of the anti-snoring device front behind the teeth. The bite strip is preferably configured, in accordance with the tooth contour, as a quarter-circle, the projections proceeding therefrom forming a shield with an approximate height of 2.5 cm and thus corresponding to the average exposed height of the back sides of the teeth. The lateral extent of the shield extends approximately to a point in front of the molars. The front cover plate is preferably approx. 3 cm high, and extends laterally to a point approximately in front of the front molar teeth.

The material used for the anti-snoring device is preferably a thermoplastic material that possesses an adhesive effect in the non-plasticized state. The anti-snoring device can be made, for example, from Thermolyn-Pedilon® or from Polysplint®. Alternatively, a two-component material can be used, the one material being plastically deformable and capable of being brought, by the addition of a further material, into a substantially rigid state.

With regard to further advantageous embodiments of the invention, reference is made to the dependent claims and to the description below of an exemplary embodiment referring to the appended drawings, in which:

Anti-snoring device 1 depicted in the Figures substantially comprises a cover plate 2 that has a curved shape such that after insertion into the space between the jaws and lips, substantially all the teeth, including the external molars, are covered.

Figure 1:
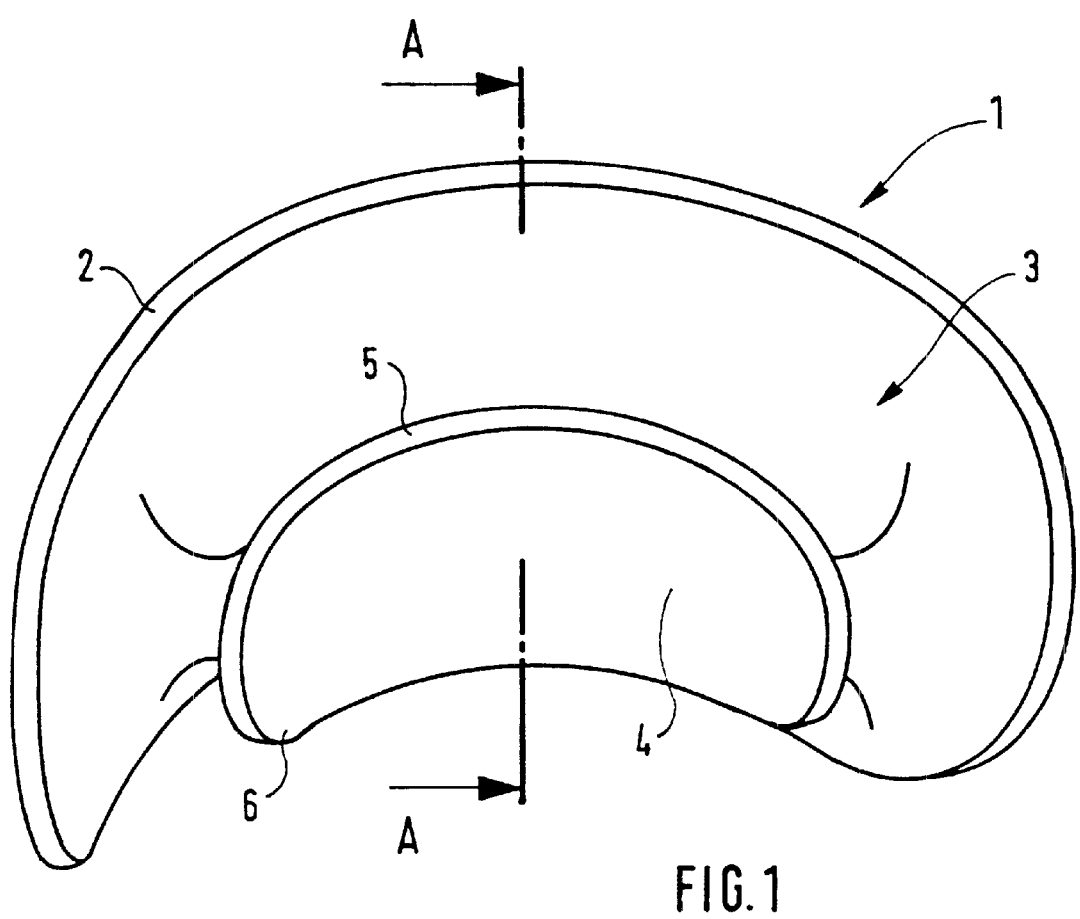
FIG. 1 shows an embodiment of an anti-snoring device according to the present invention in a perspective view.
Figure 2:
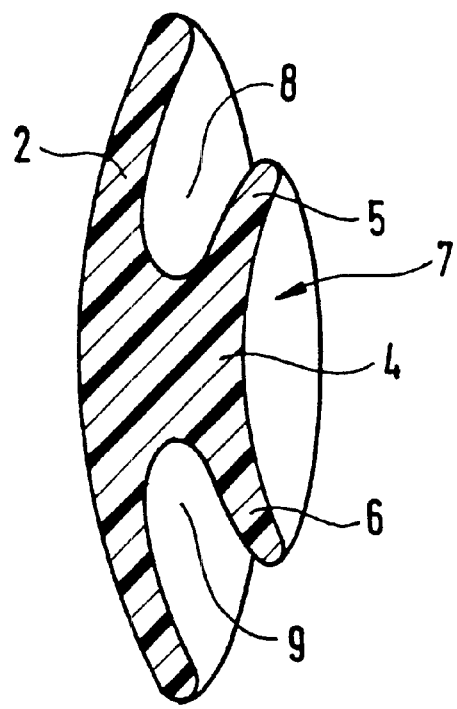
FIG. 2 shows the anti-snoring device of FIG. 1 in a section along plane A—A.
Figure 3:
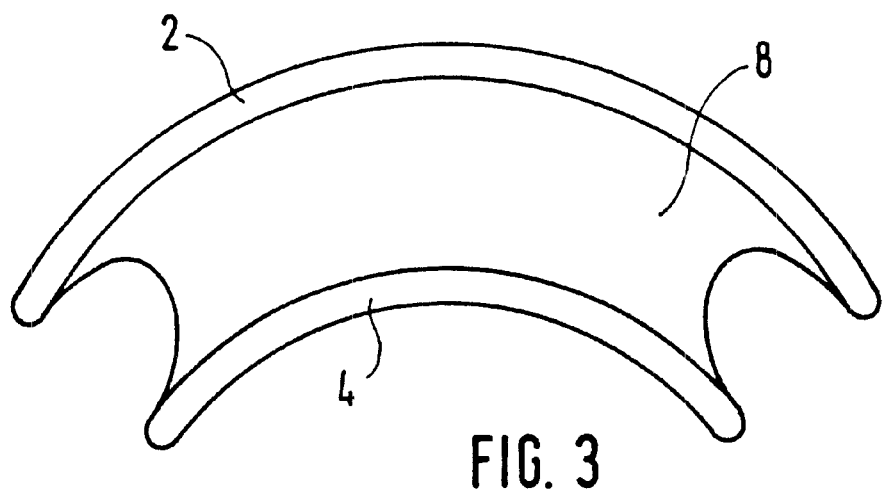
FIG. 3 shows the anti-snoring device of FIG. 1 in a plan view.

On concave side 3 of the cover plate, a bite strip 4 projects out in the region of the center plane. As shown in particular by FIGS. 3 and 4, bite strip 4 is configured, in accordance with the tooth contour, approximately as a quarter-circle, and is approximately 1 cm wide. Shaped onto bite strip 4 are lingually and palatally directed tooth retaining flanges 5, 6 which form a shield 7 that has a height of approximately 2.5 cm and a thickness of approximately 3 mm. Tooth retaining flanges 5, 6 extend substantially parallel to concave side 3 of cover plate 2, creating spaces 8, 9. When anti-snoring device 1 is inserted, the upper and lower rows of teeth fit into these spaces 8, 9 respectively. What is important here is that the lingual tooth retaining flange 6 engages behind the teeth of the lower jaw, and holds the lower jaw in a position that is pulled forward with respect to its normal position, in such a way that the incisors of the upper and lower jaws are located substantially opposite one another. The result of this action is that in a supine position, the lower jaw is retained in its pulled-forward position, so that the respiratory passages can be kept open and snoring can thus be prevented.

Anti-snoring device 1 is made entirely of a thermoplastic with a low softening temperature that is substantially rigid at ambient temperature and possesses an adhesive effect. Anti-snoring device 1 can be made, for example, of Thermolyn-Pedilon® or Polysplint®. Placing anti-snoring device 1 in hot water causes the material to become plastically deformable. After the outer surface of anti-snoring device 1 has been cooled off by immersion in cold water, so that the user cannot be burned, it is inserted into the mouth. The internal temperature of anti-snoring device 1 is still sufficiently high that sufficient molding of the form is possible. After introduction of the soft form into the mouth, a deep impression is made into the soft material, in such a way that the incisors, canines, and optionally also the molars remain inserted deeply into the material of bite strip 4, without biting through the material. The material (also soft) of cover plate 2 is then pressed against the front side of the teeth and gums and molded onto them, and in the same fashion the material of projections 5, 6 is pressed out on the inside with the tongue, against the back sides of the teeth and against the gums, into a curved plate a few millimeters thick. This molding operation involving biting and pressing results in intimate enveloping of the upper and lower rows of teeth, on both the inside and outside. Following cooling of the material, which should substantially not shrink and also not expand so that the material remains in contact against the teeth even after cooling, the teeth can be removed from the exact negative mold of the jaws only by vigorously and deliberately opening the jaws. Small amounts of shrinkage are compensated for by the fact that the material itself still possesses a certain adhesive effect.

The almost airtight enclosure of the lower and upper jaw teeth and of the gums adjacent thereto in a block of material prevents the teeth from sliding involuntarily apart, and thus prevents the tongue and lower jaw from sliding back. The lower jaw is thereby nondisplaceably immobilized, even when the muscles are relaxed, in a thrust-forward and closed state.

The almost airtight enclosure also makes it possible to immobilize the tip of the tongue by way of a suction reflex against the teeth and the curved shield 7, so that it rests in relaxed fashion in the mouth, thereby diminishing the user's tendency unconsciously to pull the tongue back against the suction effect.

A breathing hole in the anti-snoring device is not necessary. Excess material can be removed, for example, by cutting it off with scissors.

In summary, what is achieved by way of the configuration according to the present invention is to make possible, and with a small amount of applied material, lip closure in front of the teeth and a suction reflex behind the teeth. Both characteristics keep the respiratory airflow free of constricting soft tissues in the pharynx region as far as the larynx, so that snoring is reliably prevented.

What is claimed is:

1. An anti-snoring device (1) with a curved cover plate (2) having a convex and a concave side (3) which is insertable into the space between the lips and teeth of a person in order to cover the tooth spaces, there being configured on the concave side (3) a lingually directed projection (6) as well as a palatally directed projection (5) which, in the inserted state, engage behind the teeth of the upper and lower jaws, and the material of the anti-snoring device being made at least locally of a plasticizable material, so that the cover plate (2) as well as the projections (5, 6) can be pressed intimately against the tooth surfaces by tongue pressure or finger pressure, characterized in that the cover plate (2) as well as the projections (5, 6) are configured such that they envelop both the teeth and the regions of the gums adjacent thereto, and are made of a material that possesses an adhesive effect in the non-plasticized state.

2. The anti-snoring device as defined in claim 1, characterized in that at least the projections (5, 6) as well as the cover plate (2) are made of a material that is plasticizable by the action of heat, and are configured such that in the heated state they are deformable by tongue pressure and can be pressed intimately against the tooth surfaces as well as the gums.

3. The anti-snoring device as defined in claim 2, characterized in that the anti-snoring device is made of Thermolyn-Pedilom material.

4. The anti-snoring device as defined in claim 2, characterized in that it is made of Polysplint material.

5. The anti-snoring device as defined in claim 1, characterized in that the projections (5, 6) as well as the cover plate (2) are made of a material that can be converted, by the addition of a hardener, from a plastically deformable state into a substantially rigid state.

6. The Anti-Snoring device as defined in claim 1, characterized in that the lingual projection (6) is configured so that in the inserted state it engages behind the teeth in the lower jaw in such a way that the lower jaw is held in a position pulled forward with respect to its normal position.

7. The anti-snoring device as defined in claim 1, characterized in that the projections (5,6) form an arc-shaped shield (7) that is joined to the cover plate by a bite strip (4).

8. The anti-snoring device as defined in claim 7, characterized in that the shield (7) has a thickness of approximately 3 mm.

9. The anti-snoring device as defined in one of claim 7, characterized in that the shield (7) possesses a height of approximately 2.5 cm.

10. The anti-snoring device as defined in claim 1, characterized in that it is made of a two-component material.

11. A method for molding an anti-snoring device (1) with a curved cover plate (2) having a convex and a concave side (3) which is insertable into the space between the lips and teeth of a person in order to cover the tooth spaces, there being configured on the concave side (3) a lingually and a palatally directed projection (5, 6) which, in the inserted state, engage behind the teeth of the upper and lower jaws, the anti-snoring device being inserted in a plastically deformable state into the upper and lower jaws, the cover plate (2) as well as the projections (5, 6) being pressed against the teeth of the lower and upper jaws and the anti-snoring device (1) then being solidified, characterized in that the cover plate (2) as well as the projections (5, 6) are molded on in such a way that they envelop the teeth as well as the gum regions adjacent thereto, and what is used for the anti-snoring device (1) is a material that possesses an adhesive effect in the solidified state, so that it adheres to the teeth and gums.

12. The method as defined in claim 11, characterized in that a thermoplastic material with corresponding adhesion properties is used for the anti-snoring device.

13. The method as defined in claim 12, characterized in that an anti-snoring device (1) made of Thermolyn-Pedilon material is used.

14. The method as defined in claim 11, characterized in that Polysplint is used as the thermoplastic material.

* * * * *